United States Patent [19]
Heymés et al.

[11] 4,065,460
[45] Dec. 27, 1977

[54] 4,5,6,7-TETRAHYDRO-THIENO[3,2-c]-PYRIDINE DERIVATIVES AND PROCESS FOR THEIR PREPARATION

[75] Inventors: Alain Heymés, Portet-sur-Garonne; Jean-Pierre Maffrand, Toulouse, both of France

[73] Assignee: Parcor, Paris, France

[21] Appl. No.: 674,734

[22] Filed: Apr. 6, 1976

[30] Foreign Application Priority Data
May 28, 1975    France ................................ 75.16635

[51] Int. Cl.² ........................................... C07D 513/04
[52] U.S. Cl. ............................... 260/294.8 C; 424/256
[58] Field of Search ...................... 260/294.8 C, 290 P; 424/263

[56] References Cited
PUBLICATIONS
Burger, Medicinal Chemistry, Third Edition, Part II, Wiley–Interscience Pub., pp. 956–957 (1970).
Fieser & Fieser, Advanced Organic Chemistry, Reinhold Pub., pp. 634–635, (1961).

Primary Examiner—Alan L. Rotman
Attorney, Agent, or Firm—Young & Thompson

[57]    ABSTRACT

This invention relates to 4,5,6,7-tetrahydro-thieno[3,2-c]-pyridine derivatives, having the formula:

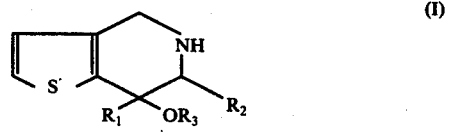

(I)

in which $R_1$ is hydrogen or alkyl having 1–6 carbon atoms; $R_2$ is hydrogen, an alkyl group having 1–6 carbon atoms or a phenyl or benzyl radical; $R_3$ represents an alkyl group having 1–6 carbon atoms or a benzyl radical, and their pharmaceutically acceptable acid addition salts.

Said derivatives have an anti-inflammatory and antalgic activity.

6 Claims, No Drawings

4,5,6,7-TETRAHYDRO-THIENO[3,2-c]-PYRIDINE DERIVATIVES AND PROCESS FOR THEIR PREPARATION

This invention relates to new thieno[3,2-c]pyridine derivatives, and to a process for their preparation.

Said compounds may also be used as intermediate derivatives in the synthesis of a large number of derivatives used in both the chemical and pharmaceutical industries.

The new compounds of this invention have the following general formula:

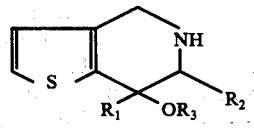
(I)

in which $R_1$ represents hydrogen or a lower alkyl group; $R_2$ represents hydrogen, a lower alkyl group or a phenyl or benzyl radical; $R_3$ represents a lower alkyl radical or a benzyl radical.

In the above formula (I) the lower alkyl and alkoxy groups contain 1–6 carbon atoms.

The invention includes also within its scope the acid addition salts of the derivatives of the formula (I) with pharmaceutically acceptable inorganic or organic acids.

The invention relates also to a process for the preparation of compounds of the formula (I) as defined above, comprising condensing a derivative of the formula:

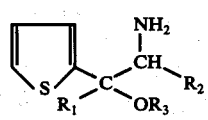
(II)

in which $R_1$, $R_2$ and $R_3$ have the above-defined meanings, with formaldehyde, to give an imine having the formula:

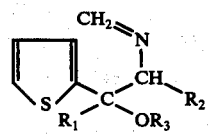
(III)

which is then cyclized to the derivative of the formula (I).

The condensation with formaldehyde may be effected in aqueous medium or within an organic solvent, such as benzene, for example. Cyclization of the imine may be effected either by action, in aqueous medium, of an organic acid (e.g., acetic acid) or an inorganic acid (e.g., hydrochloric or sulfuric acid), or by action, in anhydrous medium, and within an organic solvent such as ether, benzene or dimethylformamide, of hydrochloric acid.

The starting compounds of the general formula (II) may be obtained according to the following reaction scheme (W. H. HERZ & L. TSAI, J. Am. Chem. Soc., 1955, 77, 3529):

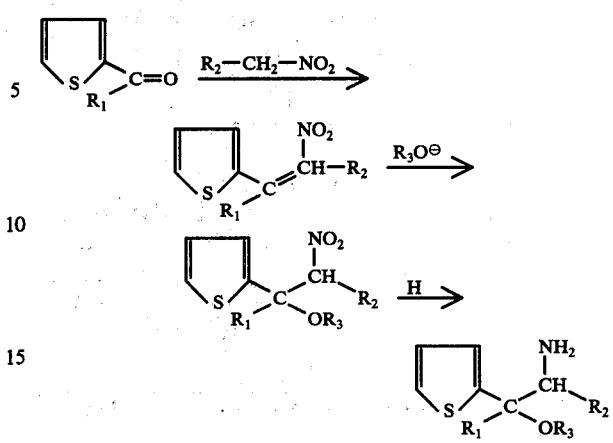

The acid addition salts of the compounds of the formula (I) may be obtained by conventional methods which will be apparent to those skilled in the art.

The following non-limiting Examples are given to illustrate the preparation of the compounds of this invention.

EXAMPLE 1

7-Methoxy-4,5,6,7-tetrahydro-thieno[3,2-c]-pyridine (Derivative n°1)

2-(2-Thienyl)-2-methoxy-ethylamine (157 g; 1 mole) is added over 2 minutes, with stirring, to a 37% aqueous formaldehyde solution (94.3 g; 1.1 mole). The temperature rises to 60° C and is maintained at this value during 90 minutes. After cooling, the reaction mixture is extracted with benzene. The organic extracts, after drying over sodium sulfate and concentration in vacuo, give the crude formimine (169 g).

To this material is added over 30 minutes, with stirring and while maintaining the temperature at 20°–30° C, 300 ml of a 6.6N solution of hydrogen chloride in dimethylformamide. The reaction medium is then left aside 90 minutes at room temperature. The resulting precipitate is filtered off, washed with acetone and dried, to give the hydrochloride (124 g), m.p. 180° C (Kofler block) (Yield: 60%).

| Analysis: for $C_8H_{12}ClNOS$ | C | H | N |
|---|---|---|---|
| Calculated %: | 46.71 | 5.88 | 6.81 |
| Found %: | 46.50 | 6.50 | 6.95 |

The compounds of following Examples 2–10 are obtained according to the same procedure.

EXAMPLE 2

| 7-Ethoxy-4,5,6,7-tetrahydro-thieno[3,2-c]-pyridine | | | |
|---|---|---|---|
| (Derivative n°2) Hydrochloride Analysis: for $C_9H_{14}ClNOS$ | C | H | N |
| Calculated %: | 49.19 | 6.42 | 6.38 |
| Found %: | 48.90 | 6.08 | 6.61 |

EXAMPLE 3

| 7-Isobutoxy-4,5,6,7-tetrahydro-thieno[3,2-c]-pyridine | | | |
|---|---|---|---|
| (Derivative n°3) Fumarate Analysis: for $C_{15}H_{21}NO_5S$ | C | H | N |
| Calculated %: | 55.03 | 6.47 | 4.28 |
| Found %: | 55.19 | 6.62 | 4.06 |

EXAMPLE 4

7-Benzyloxy-4,5,6,7-tetrahydro-thieno[3,2-c]-pyridine
(Derivative n°4) Hydrochloride
Analysis: for $C_{14}H_{16}ClNOS$

|  | C | H | N |
|---|---|---|---|
| Calculated %: | 59.66 | 5.72 | 4.97 |
| Found %: | 59.81 | 5.61 | 5.05 |

EXAMPLE 5

7-Methoxy-7-methyl-4,5,6,7-tetrahydro-thieno[3,2-c]-pyridine
(Derivative n°5) Hydrochloride
Analysis: for $C_9H_{14}ClNOS$

|  | C | H | N |
|---|---|---|---|
| Calculated %: | 49.19 | 6.42 | 6.38 |
| Found %: | 49.49 | 6.37 | 6.38 |

EXAMPLE 6

7-Ethoxy-7-methyl-4,5,6,7-tetrahydro-thieno[3,2-c]-pyridine
(Derivative n°6) Maleate
Analysis: for $C_{14}H_{19}NO_5S$

|  | C | H | N |
|---|---|---|---|
| Calculated %: | 53.66 | 6.11 | 4.47 |
| Found %: | 53.47 | 6.08 | 4.63 |

EXAMPLE 7

7-Methoxy-6-methyl-4,5,6,7-tetrahydro-thieno[3,2-c]-pyridine
(Derivative n°7) Hydrochloride
Analysis: for $C_9H_{14}ClNOS$

|  | C | H | N |
|---|---|---|---|
| Calculated %: | 49.19 | 6.42 | 6.38 |
| Found %: | 48.95 | 6.23 | 6.51 |

EXAMPLE 8

7-Ethoxy-6-methyl-4,5,6,7-tetrahydro-thieno[3,2-c]-pyridine
(Derivative n°8) Hydrochloride
Analysis: for $C_{10}H_{16}ClNOS$

|  | C | H | N |
|---|---|---|---|
| Calculated %: | 51.38 | 6.90 | 5.99 |
| Found %: | 51.12 | 6.99 | 6.21 |

EXAMPLE 9

6,7-Dimethyl-7-methoxy-4,5,6,7-tetrahydro-thieno[3,2-c]-pyridine
(Derivative n°9) Fumarate
Analysis: for $C_{14}H_{19}NO_5S$

|  | C | H | N |
|---|---|---|---|
| Calculated %: | 53.66 | 6.11 | 4.47 |
| Found %: | 53.39 | 6.43 | 4.22 |

EXAMPLE 10

7-Methoxy-6-phenyl-4,5,6,7-tetrahydro-thieno[3,2-c]-pyridine
(Derivative n°10) Hydrochloride
Analysis: for $C_{14}H_{16}ClNOS$

|  | C | H | N |
|---|---|---|---|
| Calculated %: | 59.66 | 5.72 | 4.97 |
| Found %: | 59.87 | 5.69 | 5.19 |

The results of toxicological and pharmacological tests reported below demonstrate the useful, particularly anti-inflammatory and antalgic, activities of the derivatives of this invention.

Thus, this invention relates also to a therapeutic composition having in particular an anti-inflammatory and antalgic activity, comprising, as active ingredient, a derivative of the formula (I) or a therapeutically acceptable acid addition salt thereof, together with a therapeutically administrable carrier.

TOXICOLOGICAL INVESTIGATION

Said investigation demonstrated the low toxicity and the good tolerance of the derivatives of this invention. For indicative purposes, the $LD_{50}/24hrs/kg$ of the animal, determined in Swiss mice by the intravenous route, by the method according to MILLER and TAINTER is 262 mg for derivative 1, 145 mg for derivative 2, 180 mg for derivative 3, 95 mg for derivative 4, 138 mg for derivative 5, 224 mg for derivative 6, 210 mg for derivative 7, 129 mg for derivative 8, 175 mg for derivative 9 and 195 mg for derivative 10.

PHARMACOLOGICAL INVESTIGATION

1. Anti-inflammatory Action a. Localized carrageenin-induced edema method.

0.1 ml of a 1% carrageenin solution is injected at time 0 in the metatarsal flexor muscles of the right hind limb of rats. The animals of the treated group are administered orally, additionally, 100 mg/kg of the test derivative, respectively 1 hour prior to and then simultaneously with the phlogogenic agent, and then 1 hour and 2.5 hours thereafter. The determinations effected with a ROCH micrometer at times 0, 1 hour, 2 hrs, 3 hrs and 5 hrs after carrageenin administration make it possible to determine, as a function of time, the percent anti-inflammatory activity. The results obtained are tabulated in following Table I:

TABLE I

| Derivative | Percent anti-inflammatory activity | | |
|---|---|---|---|
|  | after 1 hour | after 2 hours | after 5 hours |
| 1 | 35 | 41 | 50 |
| 2 | 36 | 44 | 52 |
| 3 | 39 | 48 | 58 |
| 4 | 42 | 50 | 60 |
| 5 | 39 | 49 | 57 |
| 6 | 40 | 49 | 61 |
| 7 | 36 | 48 | 62 |
| 8 | 38 | 53 | 61 |
| 9 | 44 | 52 | 62 |
| 10 | 37 | 50 | 56 | b. Ovalbumin-induced systemic edema method

Rats are administered a simultaneous intraperitoneal injection of 1 ml ovalbumin and 0.5 ml of a 1% Evans Blue solution. The animals of the treated group are additionally administered orally 100 mg/kg of the test derivative, one hour prior to ovalbumin administration and then simultaneously with said ovalbumin administration. The intensity of the phenomenon thus induced is rated according to a scale from 1 to 5, according to the progress of the inflammatory syndrome. The measurements are effected after 2 hours and after 3 hours. Thus are determined the mean intensity of the edema and the percent decrease of the edema reaction with respect to the control group. Said percentages are given in following Table II:

TABLE II

| Derivative | Percent decrease | |
|---|---|---|
|  | after 2 hrs | after 3 hrs |
| 1 | 51 | 60 |
| 2 | 48 | 59 |
| 3 | 51 | 63 |
| 4 | 53 | 64 |
| 5 | 49 | 60 |
| 6 | 44 | 58 |
| 7 | 47 | 58 |
| 8 | 44 | 56 |
| 9 | 50 | 63 |
| 10 | 48 | 57 |

2. Antalgic Action a. Mechanical stimulation method according to Haffner (Deutsch. Wish. 1959, 55, 731–733)

This method comprises placing a pressure forceps at the base of the tail of a mouse and recording the number of bites self-inflicted by the animal in its endeavour to remove the forceps. The decrease of the number of bites prior to and subsequently to oral administration of the test compound at a dosage of 100 mg/kg provides a measure of the antalgic activity of the derivatives of this invention. The mean percent antalgia thus determined as a function of time is given in following Table III.

TABLE III

| Derivative | mean percent antalgia | | | |
|---|---|---|---|---|
| | after 30 min. | after 1 hr | after 2 hrs | after 3 hrs |
| 1 | 75 | 63 | 59 | 51 |
| 2 | 71 | 66 | 62 | 59 |
| 3 | 68 | 60 | 55 | 48 |
| 4 | 75 | 69 | 66 | 57 |
| 5 | 67 | 61 | 55 | 46 |
| 6 | 66 | 60 | 55 | 48 |
| 7 | 70 | 65 | 61 | 53 |
| 8 | 71 | 65 | 59 | 50 |
| 9 | 68 | 63 | 56 | 49 |
| 10 | 73 | 66 | 60 | 53 | b. Acetic acid method, according to Koster, Anderson and Beer (Fed. Proced. 18., 1959, 412, 1, 626)

Intraperitoneal injection of a dilute acetic acid solution induces, in mice, characteristic writhing movements which are repeated due to the effect of pain.

Administration of derivatives of the formula (I) to the animals of the treated group, at an oral dosage of 100 mg/kg, 30 minutes prior to intraperitoneal injection of acetic acid, shows that, with respect to the untreated reference group, the number of writhing movements is markedly decreased within the next thirty minutes.

The percent antalgia thus determined is, with all the derivatives tested, greater than 60%.

The toxicological and pharmacological investigations reported above show that the compounds of this invention are endowed with a good tolerance and possess substantial anti-inflammatory and antalgic activities.

For oral administration, the composition of this invention may be formulated as tablets, coated tablets, capsules, drops and syrups. It may also be formulated for rectal administration, as suppositories and, for parenteral administration, as injectable solutions.

Each unit dose contains advantageously from 0.030 g to 0.300 g active ingredient, the administrable dosages varying within a range from 0.030 g to 0.900 g active ingredient per 24 hours.

Non-limiting Examples of pharmaceutical formulations of the composition of this invention are given below.

EXAMPLE 11

| Coated tablets | | |
|---|---|---|
| CORE | Derivative n°1 | 0.100 g |
| | Talc | 0.010 g |
| | Wheat starch | 0.025 g |
| | Magnesium stearate | 0.010 g |
| COATING | Talc | 0.010 g |
| | Potato starch | 0.015 g |
| | Gum arabic | 0.005 g |
| | Gelatin | 0.002 g |
| | Tartrazine | traces |
| | White wax | 0.001 g |
| | Carnauba wax | 0.001 g |
| | Sugar, sufficient to make 1 coated tablet | |

EXAMPLE 12

| Tablets | |
|---|---|
| Derivative N°4 | 0.100 g |
| Talc | 0.005 g |
| Starch | 0.025 g |
| Magnesium stearate | 0.005 g |
| Cellulose | 0.010 g |
| Polyvinyl pyrrolidone | 0.010 g |

EXAMPLE 13

| Capsules | |
|---|---|
| Derivative n°5 | 0.150 g |
| Magnesium stearate | 0.010 g |
| Talc | 0.010 g |
| Stearic acid | 0.005 g |

EXAMPLE 14

| Drops | | |
|---|---|---|
| Derivative n°7 | 2.00 | g |
| Flavoured excipient, to make | 30 | ml |

EXAMPLE 15

| Injectable solution | |
|---|---|
| Derivative n°10 | 0.150 |
| Isotonic solution | 5 ml |

Endowed with a very good tolerance, particularly from the digestive standpoint, the composition of this invention possesses anti-inflammatory and antalgic properties which make it usefully administrable for therapeutic purposes, both for short treatment periods and for extended treatment periods.

Having now described our invention what we claim as new and desire to secure by Letters Patent is:

1. A compound selected from the group consisting of 4,5,6,7-tetrahydro-thieno[3,2-c]-pyridine derivatives having the formula:

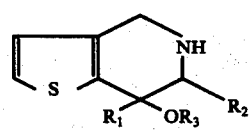

(I)

in which $R_1$ is selected from the group consisting of hydrogen and the alkyl radicals having 1-6 carbon atoms; $R_2$ is selected from the group consisting of hydrogen, an alkyl group having 1-6 carbon atoms, the phenyl radical, and the benzyl radical; $R_3$ is selected from the group consisting of an alkyl group having 1-6 carbon atoms, and the benzyl radical; and the pharmaceutically acceptable acid addition salts of said derivatives.

2. Process for the preparation of a compound selected from the group consisting of 4,5,6,7-tetrahydrothieno[3,2-c]-pyridine derivatives having the formula:

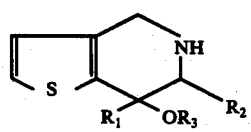

(I)

in which $R_1$ is selected from the group consisting of hydrogen and the alkyl radicals having 1-6 carbon atoms; $R_2$ is selected from the group consisting of hydrogen, an alkyl group having 1-6 carbon atoms, the phenyl radical, and the benzyl radical; $R_3$ is selected from the group consisting of an alkyl group having 1-6 carbon atoms, and the benzyl radical; and the pharmaceutically acceptable acid addition salts of said derivatives, comprising condensing a derivative of the formula:

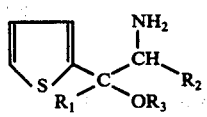
(II)

in which $R_1$, $R_2$ and $R_3$ have the above-defined meanings, with formaldehyde, to give an imine of the formula:

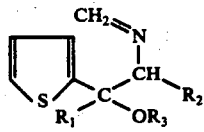
(III)

and subsequently cyclizing said imine (III) to the derivative of the formula (I).

3. Process as claimed in claim 2, wherein the condensation with formaldehyde is effected in aqueous medium.

4. Process as claimed in claim 2, wherein the condensation with formaldehyde is effected within an organic solvent.

5. Process as claimed in claim 2, wherein the cyclization of the imine is effected by action of an acid in aqueous medium.

6. Process as claimed in claim 2, wherein the cyclization of the imine is effected by action of hydrochloric acid in anhydrous medium, within an organic solvent.

* * * * *